United States Patent [19]

Immel et al.

[11] Patent Number: 5,268,509

[45] Date of Patent: Dec. 7, 1993

[54] PROCESS FOR THE PREPARATION OF AN IRON CATALYST AND A PROCESS FOR THE PREPARATION OF PRIMARY AMINES BY THE HYDROGENATION OF NITRILES USING SAID IRON CATALYST

[75] Inventors: Otto Immel, Krefeld; Dietrich Liebsch, Leverkusen; Hans-H. Schwarz, Krefeld; Stephan Wendel, Leverkusen; Peter Fischer, Odenthal-Osenau, all of Fed. Rep. of Germany

[73] Assignee: Bayer Aktiengesellschaft, Leverkusen, Fed. Rep. of Germany

[21] Appl. No.: 535,801

[22] Filed: Jun. 11, 1990

[30] Foreign Application Priority Data

Jun. 16, 1989 [DE] Fed. Rep. of Germany ....... 3919694

[51] Int. Cl.$^5$ ............................................. C07C 209/48
[52] U.S. Cl. ................................... 564/492; 534/838; 558/467; 564/461; 564/491
[58] Field of Search ............... 564/415, 490, 491, 492, 564/493, 461; 502/316, 338; 534/838; 558/467

[56] References Cited

U.S. PATENT DOCUMENTS

| | | | |
|---|---|---|---|
| 1,225,755 | 5/1917 | Bosch et al. | 502/338 |
| 3,696,153 | 10/1972 | Kershaw et al. | 260/583 |
| 3,758,584 | 9/1973 | Bivens et al. | 260/583 K |
| 3,986,985 | 10/1976 | Dewdney et al. | 564/492 |
| 4,064,172 | 12/1977 | Dewdney et al. | 260/583 |
| 4,301,032 | 11/1981 | Atkinson et al. | 252/443 |
| 4,480,051 | 10/1984 | Wu | 564/492 |
| 4,521,527 | 6/1985 | Frank et al. | 502/184 |
| 4,587,228 | 5/1986 | Frank et al. | 502/185 |

FOREIGN PATENT DOCUMENTS

| | | |
|---|---|---|
| 0848654 | 8/1950 | Fed. Rep. of Germany . |
| 848654 | 7/1952 | Fed. Rep. of Germany . |
| 1486890 | 9/1977 | United Kingdom . |
| 2092016 | 8/1982 | United Kingdom . |

*Primary Examiner*—Richard L. Raymond
*Assistant Examiner*—Peter G. O'Sullivan
*Attorney, Agent, or Firm*—Joseph C. Gil; Richard E. L. Henderson

[57] ABSTRACT

This invention relates to a process for the preparation of an iron catalyst used for the hydrogenation of organic compounds comprising partially oxidizing iron or an iron alloy in particulate form at an elevated temperature in the presence of gaseous oxygen until a weight gain of from 5% to 32% is obtained; and then reducing the partially oxidized iron or iron alloy at an elevated temperature in a stream of hydrogen.

The invention also relates to a process for the preparation of primary amines comprising catalytically hydrogenating nitriles corresponding to said primary amines in the presence of an iron catalyst of the invention.

5 Claims, No Drawings

PROCESS FOR THE PREPARATION OF AN IRON CATALYST AND A PROCESS FOR THE PREPARATION OF PRIMARY AMINES BY THE HYDROGENATION OF NITRILES USING SAID IRON CATALYST

BACKGROUND OF THE INVENTION

This invention relates to a new process for the preparation of a formed iron catalyst by partial oxidation at the surface of iron or iron alloys in the form of shavings, granulates, or other particulate form, followed by reduction by hydrogenation. This invention further relates to a process for the preparation of primary amines, in particular hexamethylenediamine, by catalytic hydrogenation of the corresponding nitriles using iron catalysts prepared by this method.

It has long been known that iron catalysts can be used for the hydrogenation of nitriles, particularly adiponitriles, to the corresponding amines. Thus, German Patentschrift 848,654 discloses a process for hydrogenating adiponitrile using an iron catalyst which has been precipitated on pumice stone and reduced at an elevated temperature. According to German Offenlegungsschrift 2,429,293, a catalyst can be prepared by melting a Swedish magnetite ore at 1590° C. After the molten iron oxide solidifies, the solid mass can be reduced in size and the resultant granulate reduced with hydrogen to yield a catalyst suitable for the hydrogenation of adiponitrile. The process for the hydrogenation of adiponitrile disclosed in German Auslegeschrift 2,034,380 also uses an iron catalyst that is prepared by reduction of a particulate iron oxide, for example, an iron ore occurring naturally in Labrador.

European Patent Application 101,584 proposes a method for hydrogenating adiponitrile using a formed iron catalyst mass containing metallic iron particles, which are obtained from anisometric iron oxide particles by hydrogen reduction. The process described for preparing the iron catalyst is relatively complicated, however, and the breakdown of the pieces obtained by compression of iron particles leads to a troublesome pressure increase when hydrogenation is carried out continuously.

It was, therefore, an object of the present invention to provide a simple process for the hydrogenation of nitriles, as well as to provide a catalyst for such a process. In particular, an object of the invention was to obtain a catalyst that could be prepared by a simple method from virtually any type of iron or iron alloy and that would combine the advantages of high activity with long service life. In addition, the difficult process of shaping the catalyst was to be avoided by using metallic iron in the form of particles suitable for heterogeneous catalytic processes.

The objects of the invention are accomplished by the processes described below for the preparation of an iron catalyst and for the preparation of primary amines by hydrogenating the corresponding nitriles in the presence of the catalyst.

SUMMARY OF THE INVENTION

This invention relates to a process for the preparation of an iron catalyst used for the hydrogenation of organic compounds comprising (a) oxidizing iron or an iron alloy in particulate form at an elevated temperature of about 200° to about 800° C. (preferably 400° to 800° C.) in the presence of gaseous oxygen until a weight gain of from at least about 5% to about 32% (preferably from 10 to 30%) is obtained, thereby forming a partially oxidized iron or iron alloy; and (b) reducing the partially oxidized iron or iron alloy at an elevated temperature of about 200° to about 500° C. (preferably 250° to 450° C.) in a stream of hydrogen, wherein said stream may contain minor quantities of non-oxidizing gases in addition to hydrogen.

The invention also relates to a process for the preparation of primary amines comprising catalytically hydrogenating nitriles corresponding to said primary amines in the presence of an iron catalyst obtained by the above process.

DETAILED DESCRIPTION OF THE INVENTION

The starting material used for the preparation of the iron catalysts according to the invention may be iron or iron alloys that can undergo oxidation with atmospheric oxygen at elevated temperatures. The preferred iron starting materials contain at least 85% by weight (most preferably at least 90% by weight) of iron. The iron may also contain minor quantities of the impurities normally present in commercial types of iron and iron alloys, such as carbon, silicon dioxide, aluminum oxide, phosphorus, calcium oxide, magnesium oxide, mangenese oxide, titanium dioxide, cobalt, manganese, chromium, and/or nickel, but must be free from substances which act as catalyst poisons. Suitable starting material for the preparation of the iron catalyst according to the invention includes commercial iron, such as shavings of C4 steel or iron sponge obtained from the so-called direct reduction of iron ore at temperatures below the melting point of the raw materials. In the process for preparing the iron catalyst, the iron or iron alloy can be used in any of a variety of particulate forms, such as a granulate, shavings, or other suitable particulate forms known in the art.

The iron is tempered at a temperature of about 200° to about 800° C. (preferably 400° to 800° C.) in the presence of gaseous oxygen, preferably air, optionally after being doped with a metal that acts as an activator, until the metal undergoes a weight increase of at least 5% and not more than 32% (preferably from 10% to 30%). This heat treatment generally requires a period of from about 5 to about 100 hours, with the time required depending, of course, on the temperature, the oxygen concentration, and the chemical composition of the iron.

The resultant partially oxidized iron or iron alloy is subjected in a second reaction step to reduction at elevated temperature in a stream of hydrogen, which may contain minor quantities of other, non-oxidizing gases such as ammonia, methane, or carbon monoxide. This reduction step is genearlly carried out at a temperature from about 200° to about 500° C. (preferably at 250° to 450° C.) under a hydrogen pressure of up to about 400 bar (preferably from 1 to 350 bar). Reduction is preferably continued until a relatively large quantity of the iron oxide formed in the first reaction step has been reduced to elementary iron. This generally takes 3 to 100 hours but a usable catalyst would still be obtained even if the iron oxide formed in the first reaction stage undergoes only partial reduction. Complete reduction of th iron oxide present is therefore not essential.

In a preferred embodiment of the process of preparation of the iron catalyst according to the invention, reduction of the oxidized iron or of the partially oxidized iron alloy takes place in the same reaction chamber as that subsequently used for hydrogenation of the nitrile. The geometrical form of the hydrogenation catalyst produced according to the present invention is basically the same as that of the iron starting material. The choice of the form of starting material may depend on the flow conditions expected in the hydrogenation reactor. This process dispenses with the procedure of separately introducing the air-sensitive catalyst into the hydrogenation reactor.

In another preferred embodiment of the process according to the invention for the preparation of the iron catalyst, the iron or iron alloy is doped with a metal that act as an activator either before or after the heat treatment but before hydrogenation. Suitable metals for this purpose include, for example, cobalt, manganese, chromium, molybdenum, ruthenium, and iridium. Doping is carried out by impregnating or moistening the iron with an aqueous solution of a salt (such as a nitrate, acetate, or formate) of the doping metal and can be carried out before or after the heat treatment. The salt-treated iron is then dried in air, optionally at an elevated temperature such as about 60° to about 120° C. The salts are generally used in a quantity corresponding to about 0.01 to about 1% by weight of the activating metal, based on the unoxidized iron or iron alloy. Doping is followed by tempering or, if doping is carried out after tempering, by hydrogenation.

The iron catalysts obtainable according to the invention are particularly suitable for use as catalysts in the hydrogenation of nitriles to the corresponding amines. The hydrogenation of adiponitrile (or hexanedinitrile) to hexamethylenediamine is particularly important industrially, but other nitriles may also be hydrogenated with the aid of a catalyst according to the invention. Suitable such nitriles include acetonitrile, propionitrile, succinonitrile (or butanedinitrile), glutaronitrile (or pentanedinitrile), benzonitrile, and nicotinonitrile (or 3-pyridinecarbonitrile).

The hydrogenation of nitriles is generally carried out in the presence of ammonia in order to prevent the formation of unwanted by-products. When ammonia is used, the nitrile (preferably adiponitrile) and ammonia are used in a ratio by weight of from 1:0.1 to 1:10 (preferably from 1:0.5 to 1:6). Hydrogenation is generally carried out at a temperature from about 80° to about 180° C. and under a pressure of from about 100 to about 450 bar. The hydrogenation may be carried out in autoclaves or in continuously operated pressure reactors, either in the presence or in the absence of solvents such as methanol, ethanol, or butanol. The primary amines (particularly hexamethylenediamine), which are generally obtained in yields of over 90% in the hydrogenation reaction, are worked up by distillation in known manner.

The following examples further illustrate details for the process of this invention. The invention, which is set forth in the foregoing disclosure, is not to be limited either in spirit or scope by these examples. Those skilled in the art will readily understand that known variations of the conditions of the following procedures can be used. Unless otherwise noted, all temperatures are degrees Celsius and all percentages are percentages by weight.

EXAMPLES

EXAMPLE 1

Commercial laboratory grade iron filings (200 g) were tempered at 600° C. for 25.5 hours in the presence of air (weight increase of 11.3%). A 30 g portion of the resultant partially oxidized iron was then reduced in a stream of hydrogen at 400° C. for 7.5 hours and after cooling was introduced into a 0.25 liter vibrating autoclave with exclusion of air. The autoclave was charged with 40 g of adiponitrile and 40 g of liquid ammonia. Hydrogen was introduced under pressure and hydrogenation was carried out for 5.3 hours at 180° C. and 250 to 300 bar. Hydrogenation yielded a reaction product containing 96.4% of hexamethylenediamine, 0.1% of aminocaproic acid nitrile, 0.48% of adiponitrile, 0.28% of 1,2-diaminocyclohexane, 1.5% of azocycloheptane, and other by-products.

EXAMPLE 2

A commercial iron granulate prepared by direct reduction of iron ore and having the following composition was used in this example:

| | |
|---|---|
| Fe: | 90–92% |
| C: | 1.5–2.5% |
| $SiO_2$: | 2.2% |
| $Al_2O_3$: | 1.0% |
| P: | 0.03% |
| CaO: | 1.1% |
| MgO: | 0.8% |
| MnO: | 0.25% |
| $TiO_2$: | 0.2% |

The granulate was reduced to a particle size of 1 to 5 mm by grinding and sieving and tempered for 22 hours in an annealing oven with access to air at an oven temperature of 620° C. (weight increase 27.7%). A 30 g sample of the tempered iron was reduced using a large excess of hydrogen (20 l/h) for 3 hours in a glass tube at 380° C.

The resultant catalyst was cooled in a stream of hydrogen and introduced into a 0.25 liter vibrating autoclave with exclusion of air. The autoclave was also charged with 40 g of adiponitrile and 40 g of liquid ammonia. Hydrogen was introduced under pressure and hydrogenation was carried out for 4 hours at 140° C. at a pressure of 230 to 300 bar, yielding a product having the following composition:

| | |
|---|---|
| hexamethylenediamine | 97.9% |
| bis(hexamethylene)triamine | 0.3% |
| azacycloheptane | 0.8% |
| 1,2-diaminocyclohexane | 0.1% |
| unknown compounds | 0.9% |

In a comparison experiment, 30 g of the same iron granulate was reduced in a stream of hydrogen at 380° C. for 5 hours without having previously been tempered. Hydrogenation of adiponitrile carried out under the same experimental conditions yielded only 18.2% hexamethylenediamine in addition to 73.8% starting material and 7.9% unidentified by-products.

EXAMPLE 3

The commercial iron granulate used in Example 2 (160.8 g) was impregnated with a solution of 20 g of water and 2.01 g of $(NH_4)_2Cr_2O_7$ and dried at 100° C.

The treated iron granulate was then tempered for 22 hours in an annealing oven with access to air at an oven temperature of 600° C. (weight increase 30%). A 28.7 g sample of the resultant material was reduced for 121 hours at 400° C. in a stream of hydrogen containing 3 vol % of ammonia.

The resultant catalyst was used for the hydrogenation of 40 g of adiponitrile in the presence of 40 g of ammonia in a 0.25 liter vibrating autoclave. The autoclave was maintained for 3.7 hours at 120° C. and 250 to 300 bar, yielding a product having the following composition:

| | |
|---|---|
| hexamethylenediamine | 98.9% |
| bis(hexamethylene)triamine | 0.2% |
| azacycloheptane | 0.5% |
| 1-2-diaminocyclohexane | 0.2% |
| unknown by-products | 0.2% |

EXAMPLE 4

A solution prepared from 1.93 g of $Ru(NO_3)_3$ and 100 g of water was added to 180 g of the commercial iron granulate used in Example 2 and the mixture was concentrated to dryness in a rotary evaporator. The dried iron granulate was then tempered for 22 hours in an annealing oven with access of air at an oven temperature of 620° C. A 41.5 g sample of the partially oxidized iron was reduced in a stream of hydrogen at 380° C. for 6 hours.

The resultant catalyst was transferred to a 0.25 liter autoclave with exclusion of air and the autoclave was then charged with 40 g of adiponitrile and 40 g of ammonia. Hydrogenation was carried out for 4 hours under a pressure of 240 to 300 bar at 120° C., yielding a product having the following composition:

| | |
|---|---|
| hexamethylenediamine | 98.5% |
| bis(hexamethylene)triamine | 0.1% |
| adiponitrile | 0.2% |
| azacycloheptane | 0.5% |
| 1,2-diaminocyclohexane | 0.2% |
| other by-products | 0.6% |

EXAMPLE 5

A 15 ml (32 g) sample of the partially oxidized iron granulate prepared in Example 2 was introduced into a vertically oriented pressure tube (diameter 14 mm, length 70 mm) for the continuous hydrogenation of adiponitrile. Hydrogen was introduced downward from above into the tube under a pressure of 280 bar and at a tube temperature maintained at 300° C. The catalyst was ready for use for the hydrogenation of adiponitrile after a reduction period of 22 hours.

Hydrogenation of adiponitrile was carried out by continuously passing a mixture of adiponitrile and ammonia in a ratio by weight of 1:1.5 to the catalyst layer from above. At the same time, the pressure in the hydrogenation apparatus was maintained at 280 bar under a constant stream of hydrogen also introduced downward from above. The liquid mixture trickled downward over the catalyst into a pressure separator. The pressure of the hydrogen was released at the top of the separator to produce a continuous stream of gas in the reaction tube. After 2016 hours at a hydrogenation temperature of 118° C. using a charge on the catalyst of 0.53 g/h of adiponitrile per ml of catalyst and a quantity of exhaust gas of 50 liters per hour, a product having the following composition was obtained:

| | |
|---|---|
| hexamethylenediamine | 98.8% |
| bis(hexamethylene)triamine | 0.6% |
| azacycloheptane | 0.2% |
| 1,2-diaminocyclohexane | 0.2% |
| unknown by-products | 0.2% |

The catalyst showed no decrease in activity after 3108 hours in operation.

EXAMPLE 6

A 15 ml (30.3 g) sample of iron granulate tempered as in Example 1 and doped with 0.5% of chromium as described in Example 3 was introduced into the pressure reactor used in Example 5 and reduced for 48 hours at a hydrogen pressure of 270 bar and at 300° C. Hydrogenation of adiponitrile was carried out at a temperature of 116° to 124° C. and a pressure of 270 bar by introducing 11.8 g of adiponitrile and 27.5 g of liquid ammonia per hour into the reactor, with release of 150 liters of hydrogen per hour in the pressure separator. A product having the following composition was obtained:

| | |
|---|---|
| hexamethylenediamine | 98.6% |
| bis(hexamethylene)triamine | 0.7% |
| azacycloheptane | 0.4% |
| 1,2-diaminocyclohexane | 0.2% |

EXAMPLE 7

A 160 g sample of the iron granulate used in Example 2 was impregnated with a solution prepared from 4.0 g of $RuCl_3$, 0.31 g of $IrCl_4.H_2O$, and 18 g of water. The impregnated iron granulate was dried at 110° C. and then tempered for 22 hours at 600° C. with access to air (weight increase 28.8%). A 30 g sample of the partially oxidized iron was reduced for 8 hours in a stream of hydrogen (30 l/h) at 400° C.

The resultant catalyst was cooled in a stream of hydrogen and introduced into a 0.25 liter vibrating autoclave with exclusion of air. After 40 g of adiponitrile and 40 g of liquid ammonia were introduced into the autoclave, hydrogenation was carried out for 190 minutes at 120° C. and 220 to 300 bar. Analysis of the reaction product by gas chromatography indicated the following composition:

| | |
|---|---|
| hexamethylenediamine | 98.2% |
| bis(hexamethylene)triamine | 0.3% |
| azacycloheptane | 0.7% |
| 1,2-diaminocyclohexane | 0.2% |
| unknown by-products | 0.6% |

EXAMPLE 8

A 160 g sample of an iron granulate having a particle size of 1 to 2 mm and the chemical composition indicated in Example 2 was impregnated with a solution prepared from 6.15 g of $Cr(NO_3)_3.9H_2O$, 0.48 g of $K_2CO_3$, and 18 g of water. The granulate was dried overnight at 100° C. and then tempered in an annealing oven with access to air at an oven temperature of 600° C. (weight increase 27.1%).

A 30 ml (61.2 g) sample of the resultant catalyst was introduced into a vertically oriented pressure tube (diameter 14 mm, length 70 cm). Hydrogen (170 l/h) was initially passed through this tube at 300° C. and 275 bar to activate the catalyst. A mixture of adiponitrile and ammonia in a ratio by weight of 1:2 was then continuously passed over the catalyst layer from above, while the pressure in the hydrogenation apparatus was maintained at 270 bar under a constant stream of hydrogen also introduced downward from above. After 230 hours at a hydrogenation temperature of 96° C. using 0.29 g/h of adiponitrile per ml of catalyst and a quantity of exhaust gas of 180 liters per hour, a product having the following composition was obtained:

| | |
|---|---|
| hexamethylenediamine | 98.8% |
| bis(hexamethylene)triamine | 0.88% |
| azacycloheptane | 0.23% |
| 1,2-diaminocyclohexane | 0.07% |
| unknown by-products | 0.12% |

After an operating time of 1156 hours, the ratio by weight of ammonia to adiponitrile was adjusted to 1.5:1 and hydrogenation was continued for an additional 46 hours at 108° C. using 0.6 g/h of adiponitrile per ml of catalyst and a quantity of exhaust gas of 80 liters per hour. The resultant hydrogenation product was found to have the following composition:

| | |
|---|---|
| hexamethylenediamine | 98.4% |
| bis(hexamethylene)triamine | 0.8% |
| azacycloheptane | 0.4% |
| 1,2-diaminocyclohexane | 0.1% |
| unknown by-products | 0.3% |

What is claimed is:
1. A process for the preparation of a primary amine comprising catalytically hydrogenating a nitrile corresponding to said primary amine in the presence of an iron catalyst, wherein said iron catalyst is prepared by a process comprising
  (a) oxidizing iron sponge, said iron sponge being obtained by direct reduction of iron ore at a temperature below the melting point of the iron ore, in particulate form at an elevated temperature of 200° to 800° C. in the presence of gaseous oxygen until a weight gain of from 5% to 32% is obtained, thereby forming a partially oxidized iron; and
  (b) reducing the partially oxidized iron at an elevated temperature of 200° to 500° C. in a stream of hydrogen.

2. A process according to claim 1 wherein the partially oxidized iron is reduced at 200° to 400° C. under a hydrogen pressure of 10 to 400 bar.

3. A process according to claim 1 wherein the nitrile is hydrogenated in the presence of ammonia at 80° to 180° C. and under a pressure of 20 to 400 bar, wherein the weight ratio of nitrile to ammonia is from 1:0.1 to 1:10.

4. A process according to claim 1 wherein the nitrile is catalytically hydrogenated in the same reaction vessel used to prepare the iron catalyst.

5. A process according to claim 1 wherein the nitrile is adiponitrile.

* * * * *